United States Patent
Ben-Haim

(10) Patent No.: US 10,672,152 B2
(45) Date of Patent: Jun. 2, 2020

(54) PROBE LOCALIZATION

(71) Applicant: Navix International Limited, Tortola (VG)

(72) Inventor: Shlomo Ben-Haim, London (GB)

(73) Assignee: Navis International Limited, Road Town (VG)

( * ) Notice: Subject to any disclaimer, the term of this patent is extended or adjusted under 35 U.S.C. 154(b) by 426 days.

(21) Appl. No.: 15/500,190

(22) PCT Filed: Jul. 30, 2015

(86) PCT No.: PCT/IB2015/055767
§ 371 (c)(1),
(2) Date: Jan. 30, 2017

(87) PCT Pub. No.: WO2016/016837
PCT Pub. Date: Feb. 4, 2016

(65) Prior Publication Data
US 2017/0263021 A1 Sep. 14, 2017

Related U.S. Application Data

(60) Provisional application No. 62/030,750, filed on Jul. 30, 2014, provisional application No. 62/030,825, filed on Jul. 30, 2014.

(51) Int. Cl.
*G06T 11/00* (2006.01)
*A61B 6/00* (2006.01)
(Continued)

(52) U.S. Cl.
CPC ............ *G06T 11/006* (2013.01); *A61B 6/037* (2013.01); *A61B 6/12* (2013.01); *A61B 6/425* (2013.01);
(Continued)

(58) Field of Classification Search
USPC .......................................... 382/128, 131–132
See application file for complete search history.

(56) References Cited

U.S. PATENT DOCUMENTS 5,077,035 A 12/1991 Wieland et al.
5,789,420 A 8/1998 Efange et al.
(Continued)

FOREIGN PATENT DOCUMENTS

CN 102120039 7/2011
EP 1733692 12/2006
(Continued)

OTHER PUBLICATIONS

International Preliminary Report on Patentability dated Feb. 9, 2017 from the International Bureau of WIPO Re. Application No. PCT/IB2015/055772. (6 Pages).
(Continued)

*Primary Examiner* — Ishrat I Sherali

(57) ABSTRACT

A method of NM image reconstruction, including:
(a) acquiring a first set of NM data of a part of the body;
(b) collecting a probe position and/or probe NM data from an intrabody probe;
(c) reconstructing an NM image from said NM data using said collected probe data.

Also described is a method of navigating to a target in a body, including:
(a) acquiring a NM image of a part of the body;
(b) collecting NM data from an intrabody probe;
(c) correlating said image and said data; and
(d) extracting location information of said probe relative to said target based on said correlated data.

29 Claims, 7 Drawing Sheets

(51) Int. Cl.
*A61B 6/03* (2006.01)
*A61B 90/00* (2016.01)
*A61B 6/12* (2006.01)

(52) U.S. Cl.
CPC ............ *A61B 6/4258* (2013.01); *A61B 6/503* (2013.01); *A61B 6/5205* (2013.01); *A61B 6/5235* (2013.01); *A61B 6/5294* (2013.01); *A61B 6/547* (2013.01); *A61B 90/39* (2016.02); *A61B 6/487* (2013.01); *A61B 6/5288* (2013.01); *A61B 6/541* (2013.01); *A61B 2090/3966* (2016.02); *G06T 2210/41* (2013.01)

(56) References Cited

U.S. PATENT DOCUMENTS

| | | | |
|---|---|---|---|
| 6,211,360 | B1 | 4/2001 | Glick et al. |
| 6,358,492 | B1 | 3/2002 | Kuhar et al. |
| 6,511,500 | B1 | 1/2003 | Rahme |
| 6,845,267 | B2 | 1/2005 | Harrison et al. |
| 7,778,685 | B2 * | 8/2010 | Evron ................ A61B 6/12 600/424 |
| 8,359,092 | B2 | 1/2013 | Hayam et al. |
| 8,364,285 | B2 | 1/2013 | Rezai |
| 9,470,801 | B2 * | 10/2016 | Ziv ................ A61B 5/055 |
| 2004/0054248 | A1 * | 3/2004 | Kimchy ................ A61B 5/055 600/3 |
| 2004/0138550 | A1 | 7/2004 | Hartlep et al. |
| 2004/0152975 | A1 | 8/2004 | Blevis |
| 2005/0008126 | A1 | 1/2005 | Juh et al. |
| 2005/0261672 | A1 | 11/2005 | Deem et al. |
| 2006/0127309 | A1 | 6/2006 | Raffel et al. |
| 2006/0287648 | A1 | 12/2006 | Schwartz |
| 2008/0230705 | A1 * | 9/2008 | Rousso ................ A61B 5/415 250/363.04 |
| 2010/0041949 | A1 * | 2/2010 | Tolkowsky .......... A61B 1/0052 600/109 |
| 2010/0221182 | A1 | 9/2010 | Purohit et al. |
| 2011/0189096 | A1 | 8/2011 | Watanabe et al. |
| 2011/0218818 | A1 | 9/2011 | Butson et al. |
| 2011/0238128 | A1 | 9/2011 | Dobak, III |
| 2012/0065492 | A1 | 3/2012 | Gertner et al. |
| 2012/0155733 | A1 | 6/2012 | Wagenknecht |
| 2012/0271171 | A1 | 10/2012 | Gertner |
| 2013/0123773 | A1 * | 5/2013 | Schwartz ............. A61B 5/7285 606/34 |
| 2014/0369560 | A1 * | 12/2014 | Wendler ............. A61B 6/4258 382/103 |
| 2015/0327805 | A1 * | 11/2015 | Ben-Haim ............. A61B 6/037 600/411 |
| 2017/0278280 | A1 * | 9/2017 | Ben-Haim ............. A61B 6/037 |

FOREIGN PATENT DOCUMENTS

| | | |
|---|---|---|
| EP | 2474526 | 7/2012 |
| KR | 20090074399 | 7/2009 |
| WO | WO 01/82978 | 11/2001 |
| WO | WO 02/102238 | 12/2002 |
| WO | WO 2009/150564 | 12/2009 |
| WO | WO 2011/091069 | 7/2011 |
| WO | WO 2013/038011 | 3/2013 |
| WO | WO 2014/115148 | 7/2014 |
| WO | WO 2014/115150 | 7/2014 |
| WO | WO 2014/115151 | 7/2014 |
| WO | WO 2014/115152 | 7/2014 |
| WO | WO 2014/141247 | 9/2014 |
| WO | WO 2015/033317 | 3/2015 |
| WO | WO 2015/033319 | 3/2015 |
| WO | WO 2015/104672 | 7/2015 |
| WO | WO 2016/016837 | 2/2016 |
| WO | WO 2016/016839 | 2/2016 |

OTHER PUBLICATIONS

International Search Report and the Written Opinion dated Jun. 5, 2014 From the International Searching Authority Re. Application No. PCT/IL2014/050086.

International Search Report and the Written Opinion dated Jun. 9, 2014 From the International Searching Authority Re. Application No. PCT/IL2014/050088.

International Search Report and the Written Opinion dated Jun. 10, 2014 From the International Searching Authority Re. Application No. PCT/IL2014/050089.

International Search Report and the Written Opinion dated May 15, 2014 From the International Searching Authority Re. Application No. PCT/IL2014/050090.

International Search Report and the Written Opinion dated Nov. 27, 2015 From the International Searching Authority Re. Application No. PCT/IB2015/055767.

International Search Report and the Written Opinion dated Jul. 28, 2014 From the International Searching Authority Re. Application No. PCT/IL2014/050246.

International Search Report and the Written Opinion dated Nov. 30, 2015 From the International Searching Authority Re. Application No. PCT/IB2015/055772.

Invitation to Pay Additional Fees dated Apr. 10, 2014 From the International Searching Authority Re. Application No. PCT/IL2014/050090.

Arora "Recent Insights Into the Role of the Autonomic Nervous System in the Creation of Substrate for Atrial Fibrillation—Implications for Therapies Targeting the Atrial Autonomic Nervous System", Circulation: Arrhythmia and Electrophysiology, XP055236980, 5(4): 850-859, Aug. 1, 2012. P.6, 7, Chapter 'Recent Developments in Imaging of the Autonomic Innervation of the Atria—Implications for AF Ablation'.

Arora et al. "Porcine Intrinsic Cardiac Ganglia", The Anatomical Record Part A, 271A: 249-258, 2003.

Burnstock "Autonomic Neurotransmission: 60 Years Since Sir Henry Dale", The Annual Review of Pharmacology and Toxicology, 49: 1-30, 2009.

Esler et al. "Sympathetic Nerve Activity and Neurotransmitter Release in Humans: Translation From Pathophysiology Into Clinical Practice", Acta Physiologica Scandinavica, 177: 275-284, 2003.

Hirsch et al. "Measuring Activity of the Autonomic Nervous System in Humans", Obesity Research, 11(1): 2-4, Jan. 2003.

IAEA "Technetium-99m Radiopharmaceuticals: Status and Trends", IAEA, International Atomic Energy Agency Radioisotopes and Radiopharmaceuticals Series, 1: 1-378, 2009.

Knuepfer et al. "Direct Assessment of Organ Specific Sympathetic Nervous System Activity in Normal and Cardiovascular Disease States", Experimental Physiology, 95(1): 32-33, 2010.

Kosa et al. "Principles and Methods of Myocardial Perfusion Imaging", Chap.2: 33-57.

Langer et al. "PET and SPET Tracers for Mapping the Cardiac Nervous System", European Journal of Nuclear Medicine and Molecular Imaging, 29(3): 416-434, Mar. 2002.

Linz et al. "Atrial Autonomic Innervation: A Target for Interventional Antiarrhythmic Therapy?", Journal of the American College of Cardiology, JACC, p. 1-33, 2013.

Malliani et al. "Emerging Excitatory Role of Cardiovascular Sympathetic Afferents in Pathophysiological Conditions", Hypertension, 39: 63-68, Jan. 2002.

Malpas "Sympathetic Nervous System Overactivity and Its Role in the Development of Cardiovascular Disease", Physiology Review, 90: 513-557, 2010.

Matsunari et al. "Iodine-123 Metaiodobenzylguanidinen Imaging and Carbon-11 Hydroxyephedrine Positron Emission Tomography Compared in Patients With Left Ventricular Dysfunction", Circulation Cardiovascular Imaging, 3: 595-603, Sep. 2010.

Mourot et al. "Effects of the Cold Pressor Test on Cardiac Autonomic Control in Normal Subjects", Physiology Research, 58: 83-91, 2009.

Rispler et al. "Quantitative 123I—MIBG SPECT/CT Assessment of Cardiac Sympathetic Innervation—A New Diagnostic Tool for Heart Failure", International Journal of Cardiology, XP028740607, 168(2): 1556-1558, Jan. 17, 2013. p. 1556, col. 1-p. 1558, col. 1.

(56) References Cited

OTHER PUBLICATIONS

Ross et al. "Research Applications of Selected [123]I-Labeled Neuroreceptor SPECT Imaging Ligands", Journal of Nucelar Medicine and Technology, 32(4): 209-214, Dec. 2004.

Sen "Some Observations of Decapsulation and Denervation of the Kidney", The British Journal of Urology, 8(4): 319-328, 1936.

Singh "Chemistry, Design, and Structure-Activity Relationship of Cocaine Antagonists", Chemical Reviews, 100: 925-1024, 2000.

Sisson et al. "Metaiodobenzylguanidine to Map Scintigraphically the Adrenergic Nervous System in Man", The Journal of Nuclear Medicine, 28(10): 1625-1636, Oct. 1987.

Smith "Extrinsic Inputs to Intrinsic Neurons in the Porcine Heart In Vitro", The American Journal of Physiology, 276(2/Pt.2): R455-R467, Feb. 1999.

Smith et al. "Simulation of Cardiovascular System Diseases by Including the Autonomic Nervous System Into a Minimal Model", Computer Methods and Programs in Biomedicine, 86(2): 153-160, May 2007.

Tan et al. "Autonomic Nerves in Pulmonary Veins", Heart Rythm, 4(3 Suppl.): S57-S60, Mar. 2007.

Travin "Cardiac Autonomic Imaging With SPECT Tracers", Journal of Nuclear Cardiology, 20(1): 128-143, Feb. 2013.

Troisi et al. "Relation of Obesity and Diet Sympathetic Nervous System Activity", Hypertension, 17(5): 669-677, May 1991.

Vallabhajosula et al. "Radioiodinated Metaiodobenzylguanidine (MIBG): Radiochemistry, Biology, and Pharmacology", Seminars in Nuclear Medicine, 41: 324-333, 2011.

Vissing et al. "Stimulation of Skin Sympathetic Nerve Discharge by Central Command", Circulation Research, 69(1): 228-238, Jul. 1991.

Wong et al. "Pericardial Fat is Associated With Atrial Fibrillation Severity and Ablation Outcome", Journal of the American College of Cardiology, JACC, 57(17): 1745-1751, 2011.

Zhang et al. "The Celiac Ganglia: Anatomic Study Using MRI in Cadavers", American Journal of Roentgenology, AJR, 186(6): 1520-1523, Jun. 2006.

* cited by examiner

PROBE LOCALIZATION

RELATED APPLICATIONS

This application is a National Phase of PCT Patent Application No. PCT/IB2015/055767, having International filing date of Jul. 30, 2015, which claims the benefit of priority under 35 USC § 119(e) of U.S. Provisional Patent Application Nos. 62/030,750 and 62/030,825, both filed on Jul. 30, 2014.

PCT Patent Application No. PCT/IB2015/055767 is also related to:

PCT Patent Application No. PCT/IL2014/050086 filed Jan. 24, 2014,

PCT Patent Application No. PCT/IL2014/050088 filed Jan. 24, 2014,

PCT Patent Application No. PCT/IL2014/050089 filed Jan. 24, 2014,

PCT Patent Application No. PCT/IL2014/050090 filed Jan. 24, 2014,

PCT Patent Application No. PCT/IL2014/050246 filed Mar. 11, 2014; and

PCT applications and publications IB2015/053984 (filed on May 27, 2015); WO2015/104672; WO2015/033319 and WO2015/033317.

The contents of the above applications are all incorporated by reference as if fully set forth herein in their entirety.

FIELD AND BACKGROUND OF THE INVENTION

The present invention, in some embodiments thereof, relates to navigating a probe, such as a catheter or other intrabody probe and, more particularly, but not exclusively, to determining the position and/or correct location of a probe using nuclear radiation emissions.

In some publications it is suggested to use a model of the anatomy, acquired, for example, by CT to constrain reconstruction of NM (nuclear medicine) data.

SUMMARY OF THE INVENTION

There is provided in accordance with an exemplary embodiment of the invention a method of NM image reconstruction, compromising:

(a) acquiring a first set of NM data of a part of the body;

(b) collecting a probe position and/or probe NM data from an intrabody probe;

(c) reconstructing an NM image from said NM data using said collected probe data.

Optionally, said collecting comprises collecting when contacting a boundary of a lumen by said probe. Optionally, said reconstructing comprises using said boundary location as a constraint during reconstruction. Optionally, said using as a constraint comprises assuming emissions cannot come from said lumen. Optionally or alternatively, said reconstructing comprises reprojecting said NM data using said constraint.

In some exemplary embodiments of the invention, the method comprises reconstructing in a locality of said position.

In some exemplary embodiments of the invention, the method comprises reconstructing at least a portion of a boundary of said lumen using a plurality of positions to cover at least 16 square centimeters and reconstructing comprises reconstructing an image of tissue adjacent said portion.

In some exemplary embodiments of the invention, the method comprises reconstructing at least a portion of a boundary of said lumen using a plurality of positions to cover at least 16 square centimeters and displaying a shape of said reconstruction with associated NM data corresponding thereto.

In some exemplary embodiments of the invention, said reconstructing comprises extending a model using said position of boundary.

In some exemplary embodiments of the invention, said reconstructing comprises reconstructing without a structural image.

In some exemplary embodiments of the invention, said reconstructing comprises reconstructing using a non-personalized anatomical model. Optionally, the method comprises matching said position to said model. Optionally, the method comprises estimating thickness of a wall at said boundary using said matching and wherein reconstructing uses said thickness. Optionally or alternatively, the method comprises defining a constraint for reconstructing a hot spot using said matching.

In some exemplary embodiments of the invention, the method comprises collecting both position and probe NM data. Optionally, said reconstructing comprises using said probe NM data for reconstructing. Optionally or alternatively, said reconstructing comprises using said probe NM data for identifying a hot spot. Optionally or alternatively, the method comprises reconstructing a local NM image from said position data and said NM probe data.

In some exemplary embodiments of the invention, the method comprises co-registering said probe position to said NM image. Optionally, said co-registering comprises acquiring an x-ray image of said part and of at least one marker whose position with respect to said NM data is known and registering said x-ray image to said NM data and to said probe position.

In some exemplary embodiments of the invention, no position data is collected using a position sensor. Optionally, the method comprises using said probe NM data and said NM data to estimate a position of the probe. Optionally or alternatively, the method comprises using said probe NM data to reconstruct an image.

In some exemplary embodiments of the invention, said probe is a catheter, said lumen is the heart and one or both of said NM data and said probe NM data comprises emissions from mIBG.

There is provided in accordance with an exemplary embodiment of the invention apparatus comprising circuitry with one or more inputs for receiving NM data, receiving probe position and/or NM data and reconstructing an NM image, for example, using methods as described herein. Optionally, this is provided as part of a system comprising a catheter with one or both of a radiation sensor and a position sensor.

There is provided in accordance with an exemplary embodiment of the invention a method of navigating to a target in a body, comprising:

(a) acquiring a NM image of a part of the body;

(b) collecting NM data from an intrabody probe;

(c) correlating said image and said data; and (d) extracting location information of said probe relative to said target based on said correlated data.

Optionally, said correlating comprises correlating said collected data with an expected set of measurements calculated using said NM image. Optionally or alternatively, said extracting location information comprises verifying a position of said probe. Optionally or alternatively, said extracting location information comprises selecting between alternative posited positions of said probe. Optionally or alternatively, said extracting location information comprises determining a position of said probe. Optionally or alternatively, said extracting location information comprises determining a plurality of fewer than 5 alternative positions of said probe. Optionally or alternatively, said extracting location information comprises determining a proximity to a hot spot. Optionally or alternatively, the method comprises combining said extracted information with position data provided by a position sensing system.

Optionally, said combining comprises providing a functional correction using said NM data to a physical position indicated by said positioning data.

In some exemplary embodiments of the invention, said collecting comprises collecting data with a substantially omni-directional sensor, with a directional sensitivity that is within a factor of 1:2 over all directions. Optionally, collecting comprises moving said probe to collect a non-scalar indication of NM data.

In some exemplary embodiments of the invention, said collecting comprises collecting data with an asymmetric sensor, with a directional sensitivity that is within a factor more than 1:2 for at least 1% of a field of view thereof. Optionally or alternatively, collecting comprises moving and/or rotating said probe to collect additional NM data for use in said correlating.

In some exemplary embodiments of the invention, said correlating comprises correlating based on a pattern of peaks and/or amplitude of peaks in said NM data.

There is provided in accordance with an exemplary embodiment of the invention apparatus comprising circuitry with one or more inputs for receiving NM image data, receiving probe NM data, correlating the NM data and NM image data and extracting location information of said probe, for example as described herein.

Optionally, this is provided as part of a system comprising a catheter with a radiation sensor.

There is provided in accordance with an exemplary embodiment of the invention a method of NM image reconstruction, compromising:
  (a) acquiring a first set of NM data of a part of the body;
  (b) acquiring a second set of intrabody probe positions;
  (c) reconstructing an NM image from said NM data using said collected probe data.

There is provided in accordance with an exemplary embodiment of the invention a method of functional image reconstruction, compromising:
  (a) providing a first set of anatomical data of a part of the body;
  (b) acquiring a second set of intrabody probe positions and functional data using the probes;
  (c) reconstructing an image from said functional data using said collected probe data and said anatomical data.

Optionally, said functional data comprises NM data.

There is provided in accordance with an exemplary embodiment of the invention a method of functional hybrid imaging, compromising:
  (a) acquiring a first set of functional data of a part of the body;
  (b) acquiring a second set of intrabody functional data;
  (c) reconstructing the hybrid image from said data.

Optionally, said functional data comprises NM data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system".

Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
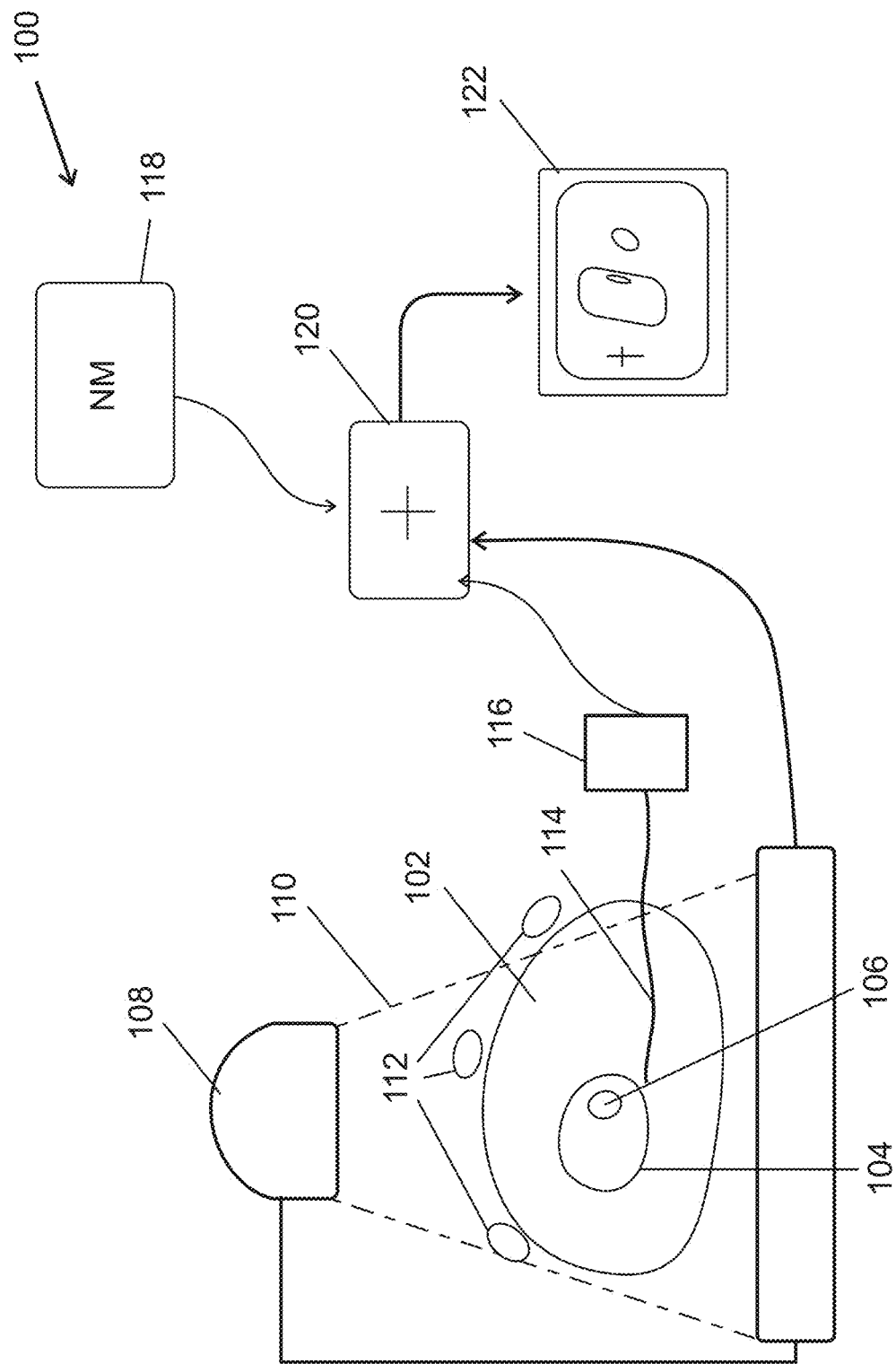
FIG. 1 is a schematic block diagram of a catheter-type probe and imaging system in accordance with some exemplary embodiments of the invention.

The present invention, in some embodiments thereof, relates to navigating a probe and, more particularly, but not exclusively, to determining the location and/or correct location of a probe using nuclear radiation emissions.

Overview

A broad aspect of some embodiments of the invention relates to using a probe position for assisting NM image reconstruction and/or for reconstruction (e.g., into an image or map) of other functional data which has a low anatomical accuracy (e.g., lower than CT, for example, lower than 10 or 5 mm voxels). In some exemplary embodiments of the invention, probe position is used to define anatomical locations which can be used to restrict reconstruction of the image so as to provide a possibly more accurate (e.g., anatomically correct) reconstruction.

In some exemplary embodiments of the invention, a plurality of probe positions are used to generate a representation of a structure of a body part. Optionally, previously and/or co-collected NM data set is registered to the representation and the representation is used to assist in reconstruction of the NM data into an image and/or into discrete data suitable for overlap on a map or other model. In one example, the representation indicates a location of walls of a body organ and the reconstruction constrains the NM data to reflect emissions from the wall, rather than from voids. Optionally or alternatively, the reconstruction is used to select data from the NM data to be used for analysis. Optionally or alternatively, the reconstruction is used to identify, in the NM data, location(s) of interest and/or indicate a desired identification of an object for the NM reconstruction, for example, the identification of a ganglion.

In some exemplary embodiments of the invention, the reconstruction does not use a previously acquired structural 3D image, such as a CT image. Optionally or alternatively, the reconstruction does not use an anatomical model.

In some exemplary embodiments of the invention, the probe positions are used to extend a previously acquired 3D image (e.g., structural and/or functional) and/or a model. In one example, the extension is by modifying the model and/or model parameters according to actual and/or current tissue shape. For example, the image and/or model is deformed and/or constrained to match measured probe locations. Optionally or alternatively, extension is in time, for example, starting from a model at one part of a cycle of deformation of an organ, probe positions measure the position of organ parts over time and show how the model is to be deformed from one state to its shape in other parts of the cycle.

Optionally or alternatively, extension is in space, for example, if the model shows only part of the organ, the positions can be used to extend the model to unmodeled portions and/or to provide more resolution within the model (e.g., between points of the model).

A broad aspect of some embodiments of the invention relates to using NM emissions to locate a catheter or other intrabody probe with respect to a navigation target.

In some exemplary embodiments of the invention, the locating comprises determining if the catheter is at an expected location.

In some exemplary embodiments of the invention, the locating comprises determining if the catheter is at and/or correctly oriented with respect to a navigation target.

In some exemplary embodiments of the invention, the locating comprises determining a general position of the catheter with respect to a navigation target.

In some exemplary embodiments of the invention, the locating comprises collecting information to assist in reconstructing an image of the target location.

In some exemplary embodiments of the invention, navigating is provided which uses both NM location information and other information, such as a previously or co-acquired image (e.g., structural and/or functional).

In some exemplary embodiments of the invention, locating uses a map of radiation emission previously or co acquired. Optionally, such a map is used to estimate what signals should be captured by an intrabody probe and/or the likelihood that captured signals reflect the target location.

In some exemplary embodiments of the invention, locating comprises locating using a position sensor on the probe which is optionally co-registered with other data.

In some exemplary embodiments of the invention, such a position sensor on the catheter is used to co-register the catheter with a co-acquired nuclear medicine image of, for example, the heart. Optionally, the patient has affixed thereto a position sensor or other marker (e.g., visible in x-ray) which is also visible in a NM imager (e.g., including radioactive material). The catheter is then used to contact various parts of an organ, e.g., the heart and collected information therefrom. In exemplary embodiments of the invention, such contacting can be used to determine a heart wall (or other lumen wall, e.g., for other organs) location. Optionally or alternatively, such contacting is used to extract from the NM image and/or NM data the expected emission to be measured by the catheter (if the catheter has a radiation sensor). Optionally or alternatively, actually measured emissions and/or determined wall locations are used to guide a reconstruction process of the NM image. In one example, the NM image is used to search for ganglions or other ANS (Autonomic nerve system) components or other parts of an image which are localized and have a relatively high (or low) activity.

For example, wall location can indicate where such a part may be physically located and thus, to be searched for, e.g., using a window on an image or data. In another example, emission measurements can be used as a seed for indicating a possible location for a ganglion.

In some exemplary embodiments of the invention, the knowledge of the probe used for sampling data and its related sensing area (e.g., a functional, $f$ which indicates a spatial behavior of sensing) are superimposed (location wise) on a co-located image, such as an anatomical image. In some exemplary embodiments of the invention, the multiple functionals, $f$, acquired at different locations and/or orientations are input into a maximal likelihood reconstruction algorithm that has the anatomical knowledge as a prior constraint and uses the set of functionals and their sampling locations to generate a reconstructed NM image of the organ.

An aspect of some embodiments of the invention relates to interplay between location information and the physical information sensed at a location. In some exemplary embodiments of the invention, the information regarding location is improved using information gathered from the physical properties at a location and/or vice versa. Optionally, multiple iterations are provided of one information improving different information.

In some exemplary embodiments of the invention, even if the position sensor is precise, if tissue moves and/or deforms, the position relative to the tissue and/or anatomical objects may be less precise, while what may be more important is the position relative to functional parts. Optionally, a functional position is used to correct/update/replace the signal.

In one example, the knowledge that a blood vessel has a wall and the fact that from physical information one can detect the location of the wall, allows one to relate to this information and use it to gain more information on the location of the probe (e.g., select between alternative probe position reconstructions), which may be useful, for example, in impedance based position sensing.

In another example, detecting that a catheter contacts a wall allows measured functional information (e.g., conductivity or radiation) to be reconstructed more accurately.

In some exemplary embodiments of the invention, the gain of information from the location or the physical property at a location can be further augmented if there is a co-registered set of anatomical information (such as a CT or an MRI). However, in some embodiments of the invention, what is used are rules, for example, that blood vessels are cylindrical and/or general anatomical models, such as the general layout and diameter of blood vessels and/or other hollow organs. Optionally or alternatively, conductivity is used to distinguish walls from blood, based on a threshold value or other method which distinguishes between values representative of wall tissue and values representative of blood.

In some embodiments, the bifurcations of blood vessels (e.g., as detected using a position sensor) is used to identify a location where the anatomical constraints (e.g., used to constrain a position reconstruction of the probe) change (e.g., more than one cylindrical lumen to be in).

An aspect of some embodiments of embodiments of the invention relates to reconstructing a functional image (e.g., NM) using both data acquired from outside the body and data acquired from inside the body. In exemplary embodiments of the invention, the data acquired inside the body is acquired using a probe and is used to enhance data acquired from outside the body. Optionally, position sensing of the probe is used to correlate the two types of data and/or to help reconstruct one or both types of data.

In some exemplary embodiments of the invention, the data acquired from outside the body and the data acquired from inside the body are of different modalities.

Optionally or alternatively, the data is of a same modality but of a different type, for example, NM data using different tracers and/or acquired at different physiological states.

An aspect of some embodiments of the invention relates to functional image reconstruction from functional data using a plurality of probe positions. Optionally, the functional data is acquired by the probes. Optionally or alternatively, the functional data is acquired using a different imager on the same patient. For example, an external NM imager may be used, for example an imager with detectors which can be brought close to the tissue being imaged.

In some exemplary embodiments of the invention, the probe positions are used to define one or more anatomical restrictions on reconstruction. Optionally, these restrictions are also defined using separately provided anatomical data (e.g., images, models, rules, from same and/or other patients). Optionally, the provided anatomical data is used as a model to be corrected by said probe position data. Optionally or alternatively, the anatomical data is used to improve positioning data of the probes.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System

FIG. 1 is a schematic block diagram of a catheter and imaging system 100 in accordance with an exemplary embodiment of the invention.

A patient 102 includes a heart (or other organ) 104 with a target 106 characterized by a radioactive emission when patient 102 is injected with a suitable radioactive marker.

An optional x-ray imager 108 (e.g., a fluoroscope) acquires an image of patient 108 with a field of view 110 and optionally one or more radio-opaque markers 112. As noted below, markers 112 may also be radioactive.

In an exemplary embodiment of the invention, system 100 is used with a catheter 114. A position sensing system 116 may be used to determine the position of catheter 114 (e.g., a tip thereof) and/or of other parts of system 100, such as markers 112 (e.g., by touching a position sensor there to, or if they include a position sensor).

NM (Nuclear medicine) data 118 may be provided, for example, from storage and/or using a NM imager (not shown). Optionally, the NM imager is used while catheter 114 is inside patient 102.

A processor 120 optionally analyses an acquired image from x-ray imager 108 for detecting markers 112 therein and optionally is used (e.g., as described below) to register the NM data to the catheter location and/or x-ray image. Optionally or alternatively, for example, as described below, processor 120 reconstructs a NM image from NM data 118, using positions indicated by position sensing system 116. In some exemplary embodiments of the invention, only processor 120 is provided and the other components are standard components.

A display 122 optionally shows one or more of a reconstructed NM image, catheter position (e.g., in space) location (e.g., relative to anatomical locations) and/or the image from imager 108.

Exemplary Catheter

Figure 2:
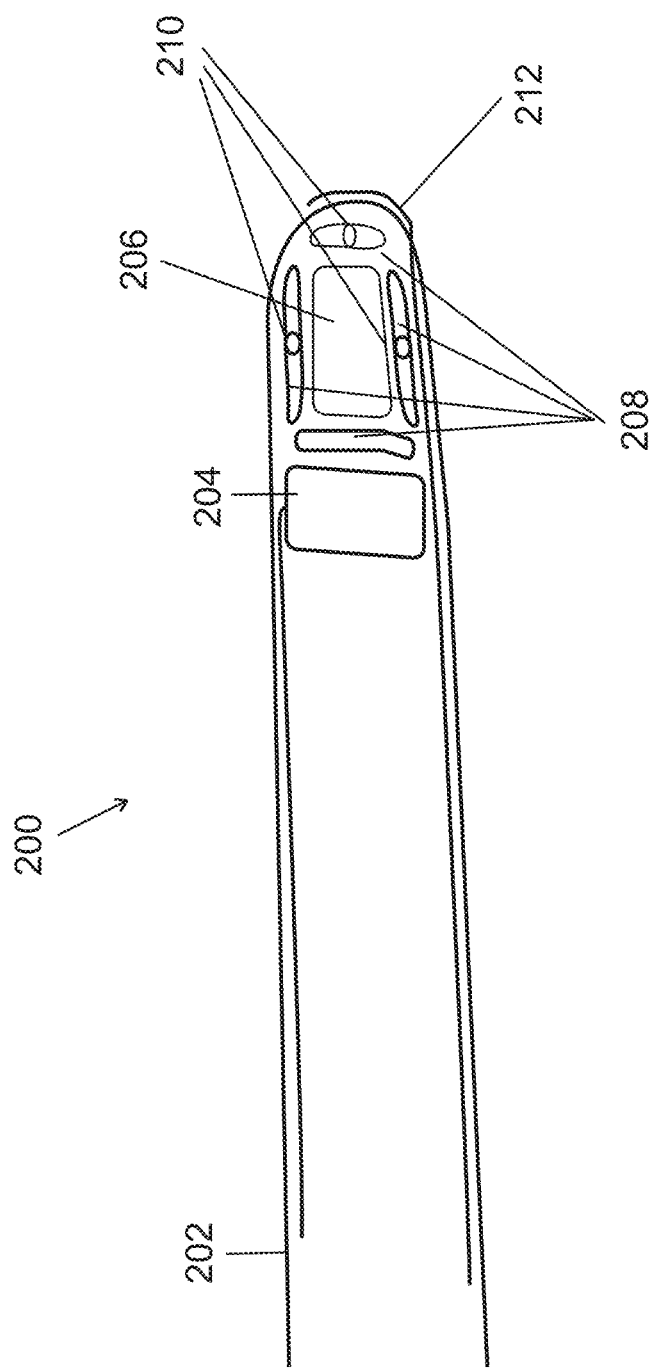
FIG. 2 is a schematic showing of a catheter for use in the system of FIG. 1, in accordance with some exemplary embodiments of the invention.

FIG. 2 is a schematic showing of a catheter 200 for use in the system of FIG. 1, in accordance with some exemplary embodiments of the invention. Optionally, catheter 200 is designed for traveling in blood vessels, for example, including a hydrophobic coating and/or has a suitable diameter (e.g., less than 5 mm, 3 mm, 2 mm or intermediate or greater sizes) and/or a suitable length (e.g., between 10 cm and 300 cm, for example, between 50 and 250 cm). Optionally or alternatively, catheter 202 is in the form of an endoscope (e.g., and may include an imager thereon), for example, for traveling through natural and/or unnatural voids in the body. Other intrabody probes (e.g., flexible, bendable and/or rigid), may be used instead of a catheter, for example, a colonoscope or other imaging probe.

As shown, catheter 200 has a body 202 and one or more components, optionally at or near its distal tip. In an exemplary embodiment of the invention, an optional position sensor 204 (e.g., a magnetic field sensor as used in the Biosense-Webster CARTO® system), is provided. Optionally or alternatively, one or more electrodes 212 is provided, for sensing and/or for stimulating tissue. Optionally or alternatively, other tools, for example, one or more of a biopsy snare, injection catheter, cryo-catheter or probe, and microwave probe or catheter, are provided.

Optionally or alternatively, a radiation sensor 206 is provided. Optionally, radiation sensor 206 is an omni-directional sensor. Optionally or alternatively, sensor 206 includes shielding 208 at one or more sides thereof, and/or is otherwise configured have a non-spherical sensitivity. Optionally or alternatively, shielding 206 includes apertures 210 (optionally shielding 208 being in the form of collimators), to provide (relatively) narrow field sensitivity. Optionally, the detector has a factor of sensitivity of greater than 1:1.5, 1:2, 1:4, 1:6, 1:10 or intermediate factors between different directions of viewing, for at least 10% (vs. a different 10%) of a surface area of the detector.

Optionally, the various sensors and/or electrodes communication using a wire or bundle that runs along catheter body 202.

In some embodiments position is detected using non-sensing methods, for example, by extracting catheter position for one or more x-ray images or by analyzing signals injected by the electrode and detected using one or more surface electrode.

Exemplary Registration

Figure 3A:
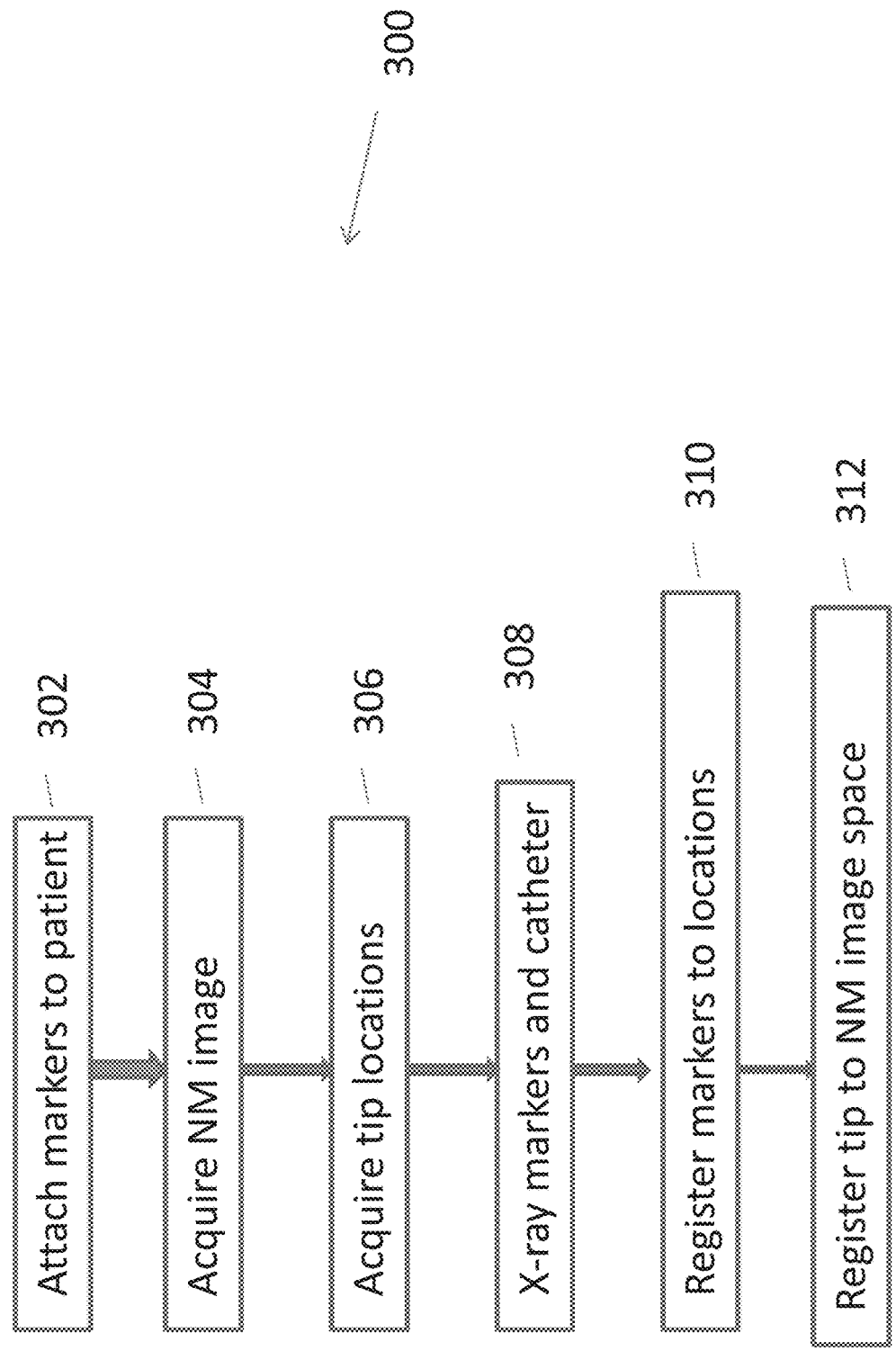
FIG. 3A is a flowchart of a method of registration using the system of FIG. 1, in accordance with some exemplary embodiments of the invention.

FIG. 3A is a flowchart 300 of a method of registration using the system of FIG. 1, in accordance with some exemplary embodiments of the invention.

At 302, one or more markers are optionally attached to patient 102. Optionally, the markers are both radio-opaque and radioactive. Optionally, the markers include a position sensor therein. Optionally, markers as described in co-filed application of same date and inventor Ben-haim with PCT Patent Application No. PCT/IB2015/055772 filed Jul. 30, 2015, now published as WO2016/016839, and which entered National Phase as U.S. patent application Ser. No. 15/500,189, filed Jan. 30, 2017, published as 2017-0278280-A1, are used, which include both a radio-opaque section and a radio-active section (optionally removable).

At 304, an NM image of the patient is acquired. Optionally, the NM image is registered to body coordinates using the markers. Optionally or alternatively, other registration methods are used, for example, using a transmission CT image. However, a particular feature of some embodiments of the invention is that no CT image is acquired, thus potentially reducing the patient radiation load.

At 306, a catheter (e.g., catheter 200) is used to acquire locations at a plurality of reference points (e.g., in the heart, two or three or more of LSPV, LIPV, RSPV, RIPV, LV Apex). In an exemplary embodiment of the invention, the locations are acquired by navigating the catheter to a location and then "capturing" and "naming" the position of the catheter to processor 120.

At 308, the catheter and markers are optionally imaged using an x-ray imager. In some embodiments, no X-ray imaging is used and, for example, the markers need not be radio-opaque. Instead, the positions of the markers are registered to the position sensor, for example by contacting of the catheter or a different position sensor thereto.

At 310, the positions of the markers is acquired, for example, by contacting with a position sensor (e.g., optionally before 308 or 306).

At 312, the NM data can be registered to the x-ray image, markers and/or position sensing space, using the above measurements. In an exemplary embodiment of the invention, this registration is used to register the instant catheter tip location to the NM data space.

In some exemplary embodiments of the invention, other registration methods are used to register the NM data space to the location of the catheter tip. In one example, position sensing is replaced or enhanced by a method of tracking displacement whereby an integration of 3D displacements from a known location are used to determine a current location. Optionally, this displacement is periodically zeroed by returning the catheter to a known location (e.g., a fixed part, such as a valve or apex), of the heart. Optionally, the displacements are determined using a 3D accelerometer and/or gyroscope at the catheter tip, for example, using calculations of a type used in INS (inertial navigation systems).

Exemplary Image Reconstruction

Figure 3B:
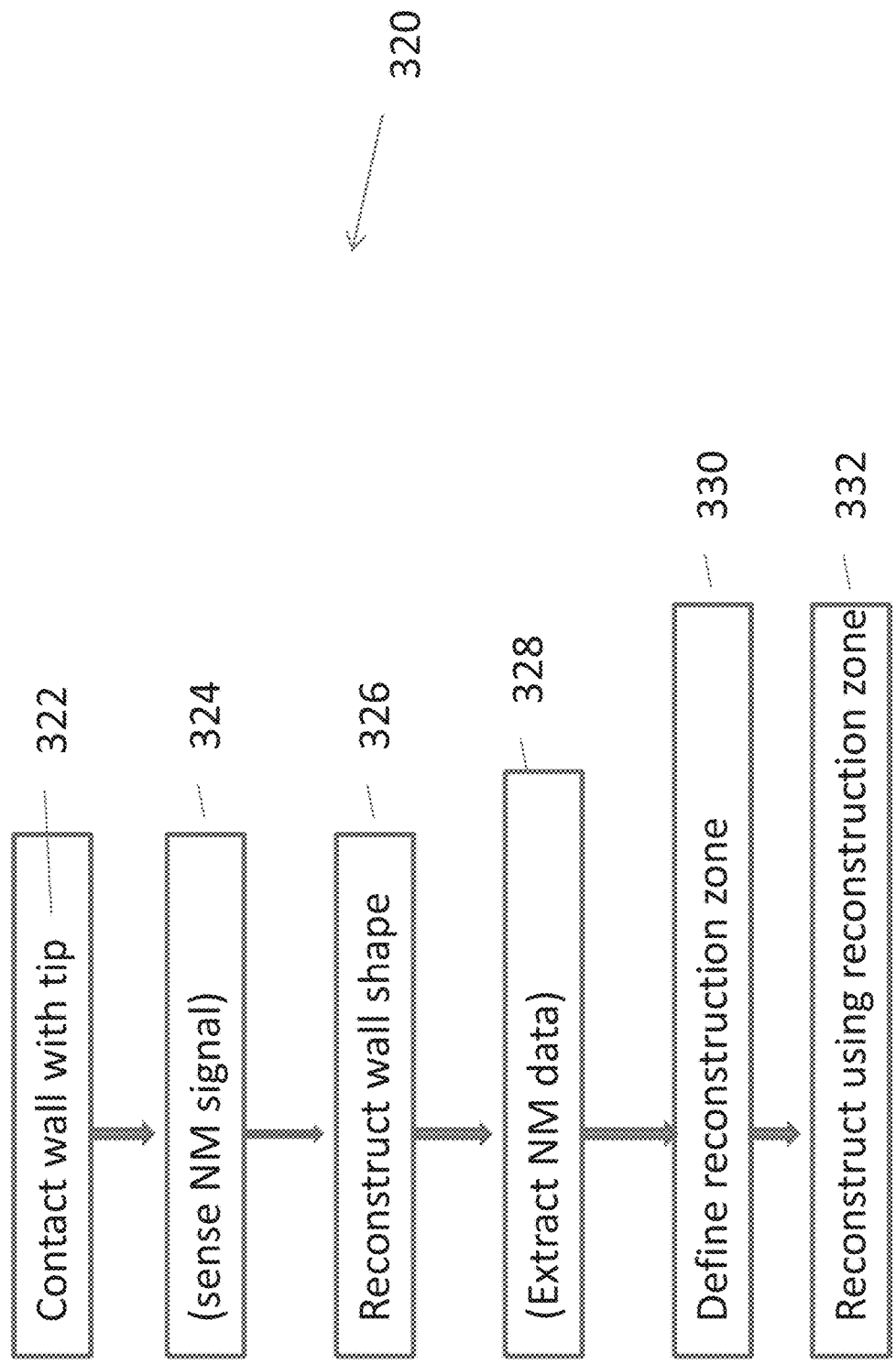
FIG. 3B is a flowchart of a method of image reconstruction using the system of FIG. 1, in accordance with some exemplary embodiments of the invention.

FIG. 3B is a flowchart 320 of a method of image reconstruction using the system of FIG. 1, in accordance with an exemplary embodiment of the invention, in which locations of the catheter tip are used to constrain NM image reconstruction, optionally by defining location where emission is expected and/or locations where emission is unexpected.

At 322, the tip (or other known part) of catheter 200 is placed against a wall or other structure from which and/or relative to which emissions are expected or expected not to be. This can be used, for example, to assess the shape of a lumen surrounding catheter 202 and/or to guide data acquisition and/or analysis, for example, as described below.

At 324, a radiation signal is optionally sensed (e.g., if sensor 206 is provided). In an organ such as the heart, signal from tissue directly adjacent the sensor and/or in its main field of view is expected to be a significant if not a majority of a signal acquired by sensor 206. If the catheter is against tissue that does not uptake the tracer, no signal from directly adjacent tissue is to be expected. Optionally, the sensed signal is marked with respect to catheter tip position and/or orientation (e.g., using position sensor 204). In some embodiments, for example, as described below, a position sensor is not provided, instead, the sensed radiation signal is used for position estimation with and/or without wall contact.

At 326, a plurality of tip positions are used to reconstruct the shape of at least part of the lumen (e.g., a heart chamber or wall section thereof, for example, a left ventricle or a left or a right atrium). Optionally, electrical sensing is used to gate the position sensing to a same part of the cardiac cycle for all measurements. Optionally or alternatively, a plurality of positions are acquired at each wall contact, allowing the location of the wall (and/or lumen shape) at different parts of the cardiac cycle to be reconstructed, optionally with measurements being binned according to cardiac cycle, extracted, for example, from ECG data and/or from change in position of the catheter within a cardiac cycle. Such windowing, triggering and/or gating is optionally and/or alternatively used also for collecting radiation information. Optionally, catheter movement within 1 second is assumed to be due to tissue movement and not due to operator movement. Optionally or alternatively, an operator can indicate when he is not providing movement, for example, using a foot control. Optionally or alternatively, a sensor in the port and/or catheter can indicate relative movement of the catheter and port. Optionally or alternatively, a sensor in a manipulator (e.g., for bending catheters) is used to detect human, vs. tissue caused movement. Optionally or alternatively, an x-ray image is analyzed to determine a cause of movement, for example, by measuring a catheter length inside the body and/or movement of a catheter tip relative to heart wall or other anatomical markers.

In an exemplary embodiment of the invention, the wall locations are used to build a mesh model of the lumen wall. Optionally, this model is correlated with a known anatomy (e.g., general human anatomy and/or a previously acquired image). Optionally, such correlation may be used to determine structural feature snot at the lumen surface, for example, wall thickness, identification of the anatomical location and/or expected nearby possibly emitting structures and/or non-emitting structures, for example, the mitral valve annulus ring will have different (if any) emitting properties and has a generally known shape. Optionally, wall thickness is used for reconstructing, for example as described below. Optionally or alternatively, anatomical location is used to refer back to an anatomical model which may be used, for example, for navigation and/or diagnosis (e.g., with the data projected onto such a model, rather than using only the acquired mesh). Optionally, the anatomical model is modified (e.g., resized, rotated and/or deformed) to match or approximate the acquired mesh model. Optionally, the deformation is local, for example, to areas of between 1 and 5 cm in diameter.

In an exemplary embodiment of the invention, the mesh has an average cell size (e.g., corresponding to spatial sampling rate) of less than 30 mm, less than 20 mm, less than 10 mm or intermediate or greater diameters, for an area of, for example, at least 10 cm^2, 20 cm^2, 40 cm^2, 80 cm^2 or intermediate mesh sizes. Optionally, the mesh cell size is selected according to a desired resolution and/or a desired motion-related accuracy. For example, mesh size may be smaller than 5 times, 3 times, 2 times, or 1 time the wall thickness. In an exemplary embodiment of the invention, the cardiac cycle is divided into at least 2, 3, 4, 5, 8 or smaller or intermediate numbers of different states. The number of states may be different for different parts of the heart, for example, fewer states where there is less data and/or less motion.

At 328, NM data correlated with the catheter tip position is optionally extracted. Optionally, a predefined shape for extraction is provided. Optionally or alternatively, a shape based on the anatomy is extracted. Optionally, the activity in this extracted portion is compared to the activity sensed by the catheter. This may be used, for example, for navigation and/or to detect changes in activity. Optionally or alternatively, the activity is displayed (e.g., color coded) on display 122, optionally overlaying the anatomical model. Optionally, local activity is activity in a cube with a width of 3 mm, length of 3 mm and height of 8 mm with respect to the tip (e.g., long axis perpendicular or at an angle to lumen wall).

At 330, a reconstruction zone is optionally defined. In some exemplary embodiments of the invention, the reconstruction zone defines the walls of the lumen, for example, based on the acquired positions and/or model. Optionally or alternatively, the reconstruction zone defines a location relative to the probe, for example, wall in contact with the probe and/or tissue on the other side of the wall.

At 332, the NM data is reconstructed using the defined reconstructed zone. In some exemplary embodiments of the invention, NM data is reconstructed and/or re-projected to be constrained to avoid the hollow of the lumen. In some exemplary embodiments of the invention, determination of the wall is used to define locations where high emitting objects (e.g., ganglions) may be located. Reconstruction comprises searched for such objects and/or determining if a reconstruction of a ganglion at such locations is reasonable. Exemplary reconstruction techniques which may be used are described in PCT publication WO2014/115148, the disclosure of which is incorporated herein by reference.

Optionally, such searching is in a volume within (for example) 1 cm distance from the lumen wall.

In some exemplary embodiments of the invention, reconstruction comprises reconstructing a locality of the probe, for example, using extracted NM data and/or sensed NM data. Optionally, such reconstruction uses the wall location to limit reconstruction from "leaking" into the lumen.

In some exemplary embodiments of the invention, the NM imaging comprises imaging using a nerve imaging agent such as mIBG, and the searching comprises searching for ganglions as being objects of a generally spherical or ellipsoid or almond like shape and a size of long axis of between 5 and 22 mm. It is noted that mIBG may also be used to detect androgenic synapses in muscle tissue, possibly indicating a level of nervous control of such tissues.

In some exemplary embodiments of the invention, the NM imaging comprises imaging using a muscle metabolic agent, such as Sestamibi and the imaging indicates the extent and/or viability of muscle, such as cardiac muscle.

In some exemplary embodiments of the invention, the NM data and the NM probe data relate to emissions of different radioactive tracers. For example, the NM data may be of Sestamibi and the probe data of mIBG. Optionally or alternatively, the NM data includes multiple tracer data. In some exemplary embodiments of the invention, the NM data is useful, for example, for navigation and/or reconstruction, as all the tracers can share of different concentration in solid tissue as compared to blood (e.g., and can be used to indicate at least part of the shape of the heart, possibly enough for model matching with boundary locations determined by the position sensor).

Optionally or alternatively, he relative positions of the two tracers may be expected, for example, mIBG concentrations being within or near viable muscle indicated by Sestamibi. Optionally or alternatively, the probe is used to identify location having a mismatch between the radiation indicated in the NM data (e.g., Sestamibi) and instant radiation (e.g., mIBG). This may indicate various pathologies, for example, as described in the above mentioned related applications, for example, WO2015/033317, the disclosure of which is incorporated herein by reference.

Exemplary Navigation

In an exemplary embodiment of the invention, NM data collected by catheter 200 is used to assist in navigating to a target and/or otherwise determining the catheter location.

Figure 4:
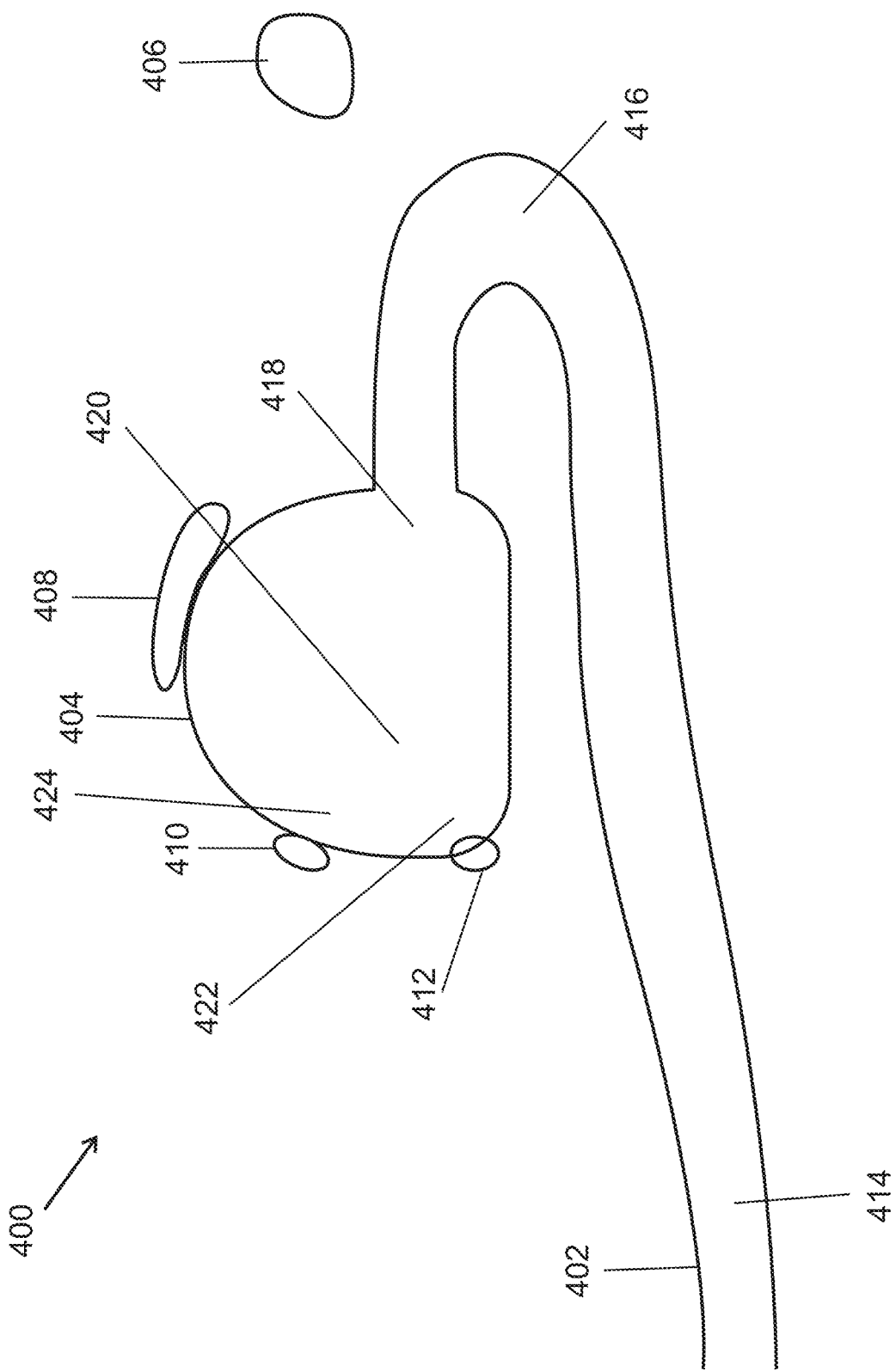
FIG. 4 is a schematic showing of navigating to a target in accordance with some exemplary embodiments of the invention.
Figure 6:
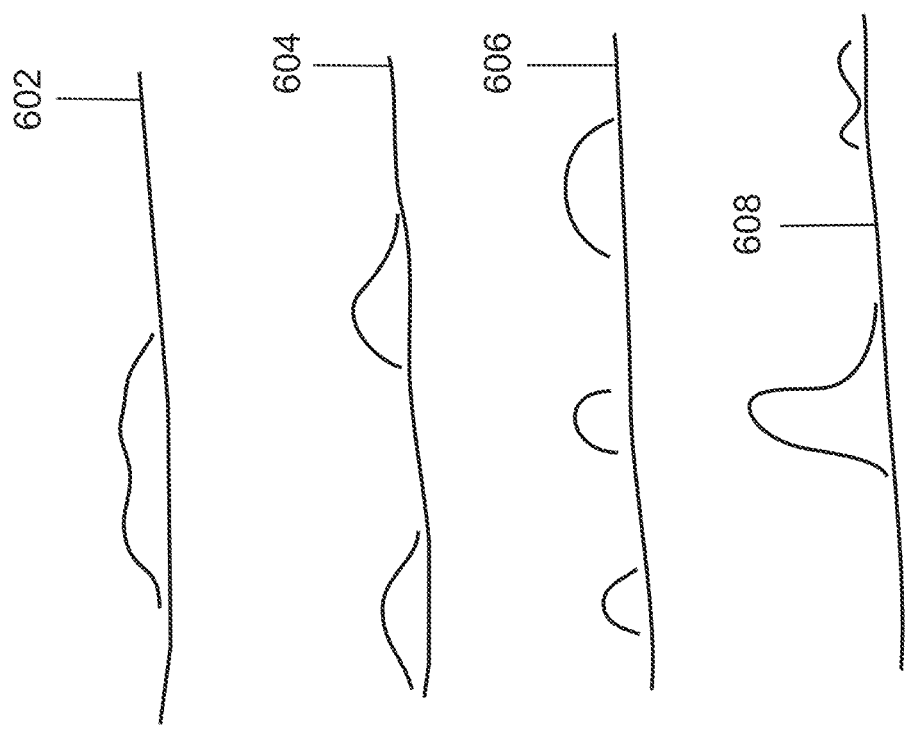
FIG. 6 is a schematic showing of signals detected by a probe following the showing of FIG. 4, in accordance with some exemplary embodiments of the invention.

FIG. 4 is a schematic showing 400 of navigating to a target in accordance with an exemplary embodiment of the invention. In the example of navigating to a hollow organ, such as a heart via the vascular system, a catheter 200 may travel along a lumen 402 (e.g., the aorta), to an organ 404 (e.g., the heart) to a target location 410 (e.g., a location to be ablated in organ 404). A probe other than catheter 200 may be used and for other organs. Also, the pathway may be via tissue or an artificial lumen, rather than natural lumens such as the vascular system or GI tract. In FIGS. 4, 412 and 408 indicate other radio-emissive locations in the organ which are not the target and a radio-emissive location 406 (e.g., the liver) which is not in organ 404. References 414-424 indicate various locations at which navigation activities are carried out in accordance with some embodiments of the invention and as described below. FIG. 6, explained below, shows radiation measurements taken at such locations, in accordance with some embodiments of the invention.

Figure 5:
FIG. 5 is a flowchart of a method of navigating using catheter based sensing, in accordance with some exemplary embodiments of the invention.

FIG. 4 illustrates various ways of navigating, one or more of which may be applied in some embodiments of the invention. FIG. 5 is a flowchart 500 of a method of navigating using catheter based sensing, in accordance with an exemplary embodiment of the invention.

At 502, the catheter location is optionally determined using a position sensor (e.g., 204). It should be noted that there are several positioning coordinates to be considered in some embodiments of the invention. One is the physical location, for example, absolute location in space and/or relative to an anatomical location, usually denoted herein as "position". Another is a functional location, relative to a function in tissue (e.g., distance from a metabolic hotspot). Such a position may also be binary, being either at the location or not. Functional location and anatomical location are usually denoted herein as "location".

At 504, a radiation signal is sensed from catheter 200. In some embodiments, the signal is scalar and indicates a strength of detected emission. This may correlate with a distance from one or more hotspots but will generally not give direction.

Optionally, the catheter is moved, so as to provide multiple such measurements, optionally using a position sensor and/or measurement of change in catheter insertion, to build a spatial or linear map of different measurements at different locations. Optionally or alternatively, the catheter is asymmetrically sensitive and is optionally rotated so as to provide different measurements from different directions.

At 506, expected measurements are determined. For example, he expected radiation measurements may be calculated from the position of the catheter, the detector spatial sensitivity and a previously or co acquired NM data set. Optionally, the data set is corrected for an effect of delay between imaging and catheter navigation, for example, using models of tracer redistribution and/or decay. Optionally or alternatively, catheter measurements (or measurements with a different radiation sensor, for example, near the heart and/or the liver, optionally from outside the body) at one or more locations are used to normalize the NM data model.

In some cases location data is used. For example, using a previously or co-acquired structural data, an expected position of the catheter (e.g., "should be within aorta") is provided. Optionally, the position data (e.g., a series of locations and/or orientations) is used to detect motion along a straight and/or curved and optionally constricted pathway (e.g., a particular blood vessel as an example of a pathway with a generally known geometry), for example, detecting the traversal of an aortic arch based on a 180 degree change in catheter path and a suitable bending radius.

At 508, the expected data is correlated with the measured position and/or radiation data. The correlation may be used, for example, to find a correct match, to find a best match and/or reject matches.

At 510, in some exemplary embodiments of the invention, a correct match is optionally used to determine a location of the catheter based on matching of data to the expected data associated with a certain position (e.g., verification). Optionally or alternatively, a correct match is used by searching the space of possibilities for a position where the measurements match the expected data. This may be used to find a location. Various search mechanism may be used, including, for example, pattern matching and a priori-reduction of possible matches by processing the data to extract one or more features which are expected in the measured data.

In some exemplary embodiments of the invention, a correct match is used to verify if the catheter is at an expected location or not. Optionally, any match below a threshold is indicated as a failure.

In some exemplary embodiments of the invention, a best match is used to estimate a catheter position. Optionally, matching comprises using both position data and radiation data, for example, weighted and/or cross-verified (e.g., a match is considered only if both position and radiation data meet certain quality criteria).

Optionally or alternatively, a best match is used to decide between a small number of alternative navigation options. For example, a best match may be used to indicate if the catheter is in one heart chamber or another, or if the target is generally to the right or to the left.

Referring back to FIG. 4 for examples or using position data and/or radiation data, at 414, radiation data may be unable to indicate more than a very general position. Position data may indicate if the catheter left vessel 402 to a branching vessel.

At 416, position data may indicate the curve in travel and radiation sensing may indicate a proximity to radiation sources and/or the general spatial distribution of 406 on one side and 408-412 on the other side of the position.

At 418, as organ 404 is entered, position data may indicate ability to move in various directions and radiation data may indicate radiation sources at relative proximity and at various directions.

At 420, radiation measurement signals are expected to increase, indicating that even a scalar measurement of radiation signal may be used to assist in navigation (e.g., detecting increase as target 410 is approached).

At 422, near a hotspot 412 (not target 410), radiation intensity may be correct, however, position and/or radiation signals from other directions may be incorrect.

At 424, all the indicators match up. Optionally, radiation intensity is used to verify maximum proximity to a hot spot and/or guide rotation of catheter 200 so that, for example, a desired portion thereof (if any, such as an ablation mechanism) is in contact with the wall of organ 404.

Optionally or alternatively, to position data, other data may be used to assist in navigation. For example, structural data such as from a CT, ultrasound, MRI or x-ray image may be used to provide anatomical constraints on possible locations for the catheter. Optionally or alternatively, functional data, such as electric or magnetic measurements may indicate relative position on and/or distance from the wall of an electrically active organ. Optionally or alternatively, other data may be collected and/or displayed, for example, one or more of pressure, displacement, heat and/or conductivity. In an exemplary embodiment of the invention, such other data may be useful if there is a map indicating expected properties and/or values for such data at each point and/or at points of interest.

Exemplary Correlation for Navigation

FIG. 6 is a schematic showing of signals which might detected by a probe following the showing of FIG. 4, in accordance with an exemplary embodiment of the invention.

The traces shown in FIG. 6 are angular traces (2D for simplicity of showing, but may be 3D), with the x-axis being an angle (straight ahead being at the middle of the x-axis) and the y-axis indicating amplitude of signal. Noise is generally not shown, but it is noted that the signal is generally noisy, which may lead to a need to collect data over a period of time. Optionally or alternatively, data is collected as the catheter is moved and navigational conclusions updated during such movement and displayed. Optionally, a display shows both an anatomical (e.g., relative to torso markers 112 and/or internal anatomy) and/or functional position. In some embodiments, changes in functional position are used to update the displayed anatomical data (e.g., indicating that the heart moved, based on movement of hot spots thereof).

Reference 602 shows a signal as might be measured at 414. A generally low amplitude and angularly wide peak indicates the distance and spatial distribution of radiation emission targets.

Reference 604 indicates a signal as may be measured at 416, the dual peaks indicate that source 406 is to one side and sources 408-412 (not distinguished) are to another side. Based on the previously acquired model of the NM data, this suggests guiding the catheter to the left. If only a scalar signal is measured, it is expected that the measured amplitude increase towards location 416 and then decrease as the catheter moves away (possible increasing again when entering the organ).

In some exemplary embodiments of the invention, an expected measured signal may be provided by analyzing the NM data (e.g., image) and simulating a travel of the catheter in that data. Such an expected signal can be a 1D signal or a 2d or 3D or 4D signal (with one dimension being time or location along the path). Optionally or alternatively, signals expected if the catheter is incorrectly navigated are also generated. Optionally, the system can show to the user the expected signal and/or signal gradient. Optionally or alternatively, the system can generate an alert if the catheter deviates from such an expected signal, for example, using processor 120.

Reference 606 indicates a signal as may be measured when entering organ 404 and which shows peaks corresponding to each of hot spots 408, 410 and 412. In an exemplary embodiment of the invention, the relative angular position of the peaks is used to determine catheter position. It may be expected that as catheter 200 advances to location 420, the peaks will move apart and increase in intensity.

In one example, signal 606 is correlated to the NM data by generating an array of signals as expected to be measured from multiple locations in the body (e.g., locations along the path and/or with organ 404). Correlation can then be used to find one or more best and/or acceptable fits. Optionally or alternatively, expected signals are generated (and/or refined and/or searched) on the fly based on an expected and/or estimated position(s) or range(s) of positions of the catheter. In some embodiments correlation is statistical, in that different possibilities are given a different probability of being possible, based on quality of correlation and/or a model of noise in measurement and/or change in emission relative to the acquired NM data. The determined correlation may be used to select between multiple possible positions and/or narrow down the position of the catheter.

In an exemplary embodiment of the invention, radiation-based position is combined with other types of positioning. For example, electrical impedance based positioning (or other positioning methods) may be accurate with respect to the organ, but inaccurate with respect to small movements of a catheter. However, if such small movements have a significant effect on the radiation signal (e.g., emitted from a hot spot), the two signals can be combined or the radiation signal can be used to correct the impedance signal.

Even if the position sensor is precise, if organ 404 moves and/or deforms, the position relative to the organ may be less precise. A functional position may be used to correct/update/replace the signal.

In some embodiments of the invention, for example, if correlation indicates multiple possible positions for the catheter, processor 120 indicates a change in catheter position which should result in a different signal depending on the starting point of the catheter. If a user then moves the catheter, the resulting signal may then be used to further select between alternative approximations of the starting position.

Signal 608 shows a measurement at location 422, near hotspot 412. While there is a high peak, the secondary peaks are incorrectly located.

Signal 610 shows a central high peak (410) and two smaller side peaks (408, 412), smaller due to distance. Optionally, at this point catheter 200 is moved to maximize the signal. Optionally, image reconstruction, for example as described above, is applied to better image the hot spot.

General

It is expected that during the life of a patent maturing from this application many relevant nuclear medicine imaging techniques will be developed and the scope of the term NM is intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of nuclear medicine (NM) image reconstruction, compromising:
   (a) acquiring a first set of NM data of a part of the body;
   (b) collecting probe data comprising one or both of probe position data and probe NM data from an intrabody probe located in a lumen within said part of the body;

(c) reconstructing an NM image of at least some of said part of the body from said NM data using said collected probe data,
wherein using said collected probe data comprises identifying a structure of at least a part of said lumen using said probe data and wherein said reconstructing comprises using said structure as a reconstruction constraint during said reconstructing.

2. A method according to claim 1, wherein said collecting comprises collecting when contacting a boundary of a lumen by said probe.

3. A method according to claim 1, wherein using said collected probe data comprises using said collected probe data to generate a 3D map of a position of at least part of a boundary of said lumen and wherein said reconstructing comprises using said boundary location as a constraint during reconstruction.

4. A method according to claim 3, wherein said using as a constraint comprises assuming emissions cannot come from said lumen.

5. A method according to claim 3, wherein said reconstructing comprises reprojecting said NM data using said constraint.

6. The method according to claim 1, comprising reconstructing in a locality of a position of the probe when collecting probe data.

7. The method of claim 1, comprising reconstructing at least a portion of a boundary of said lumen using a plurality of positions to cover at least 16 square centimeters and reconstructing comprises reconstructing an image of tissue adjacent said portion.

8. The method of claim 1, comprising reconstructing at least a portion of a boundary of said lumen using a plurality of positions to cover at least 16 square centimeters and displaying a shape of said reconstruction with associated NM data corresponding thereto.

9. The method of claim 1, wherein said reconstructing comprises extending a model using said position of boundary.

10. The method of claim 1, wherein said reconstructing comprises reconstructing without a structural image.

11. The method of claim 1, wherein said reconstructing comprises reconstructing using a non-personalized anatomical model.

12. A method according to claim 11, comprising matching said position to said model.

13. A method according to claim 12, comprising estimating thickness of a wall at said boundary using said matching and wherein said reconstructing uses said thickness.

14. A method according to claim 12, comprising defining a constraint for reconstructing a hot spot using said matching.

15. The method of claim 1, comprising collecting both probe position data and probe NM data.

16. A method according to claim 15, wherein said reconstructing comprises using said probe NM data for reconstructing.

17. A method according to claim 15, wherein said reconstructing comprises using said probe NM data for identifying a hot spot.

18. A method according to claim 15, comprising reconstructing a local NM image from said position data and said NM probe data.

19. The method of claim 1, comprising co-registering said probe position to said NM image.

20. A method according to claim 19, wherein said co-registering comprises acquiring an x-ray image of said part and of at least one marker whose position with respect to said NM data is known and registering said x-ray image to said NM data and to said probe position.

21. A method according to claim 1, wherein no position data is collected, and said probe NM data and said NM data are used to estimate a position of the probe.

22. A method according to claim 1, wherein no position data is collected, and said probe NM data is used to reconstruct an image.

23. The method of claim 1, wherein said probe is a catheter, said lumen is in the heart and one or both of said NM data and said probe NM data comprises emissions from mIBG.

24. A method of nuclear medicine (NM) image reconstruction, comprising:
(a) acquiring a first set of NM data of a heart, the NM data comprising emissions from mIBG;
(b) collecting probe data comprising probe position data and/or probe NM data from a catheter probe in the heart; and
(c) reconstructing an NM image of at least a part of said heart from said NM data using said collected probe data,
wherein using said collected probe data comprises identifying a structure of at least a part of said lumen using said probe data and wherein said reconstructing comprises using said structure as a reconstruction constraint during said reconstructing.

25. The method of claim 24, wherein said collecting comprises collecting when the catheter probe is contacting a boundary of a lumen in the heart.

26. The method of claim 1, wherein the first set of NM data is acquired using an external imager.

27. The method of claim 1, wherein the first set of NM data is acquired using a first imager, and the probe NM data is acquired using a second imager.

28. The method of claim 1, wherein said collecting comprises collecting a plurality of probe positions using a position determining system which determines the position of the probe and using said positions for said identifying of said structure and wherein said probe does not include a radioactive emission detector.

29. The method of claim 1, wherein said collecting comprises analyzing signals injected by said probe.

* * * * *

UNITED STATES PATENT AND TRADEMARK OFFICE
CERTIFICATE OF CORRECTION

PATENT NO. : 10,672,152 B2  
APPLICATION NO. : 15/500190  
DATED : June 2, 2020  
INVENTOR(S) : Shlomo Ben-Haim Page 1 of 1

It is certified that error appears in the above-identified patent and that said Letters Patent is hereby corrected as shown below:

On the Title Page

Item (73) Assignee, Line 1, "Navis" should be changed to --Navix--

Signed and Sealed this  
Tenth Day of November, 2020

Andrei Iancu  
*Director of the United States Patent and Trademark Office*